United States Patent
Fujita et al.

(10) Patent No.: US 6,819,791 B2
(45) Date of Patent: Nov. 16, 2004

(54) COLOR IMAGE ANALYSIS METHOD

(75) Inventors: Satoshi Fujita, Nisshin (JP); Naoki Odani, Nagoya (JP); Naoto Kagiyama, Kariya (JP); Masayoshi Momiyama, Handa (JP)

(73) Assignee: Aisin Seiki Kabushiki Kaisha, Kariya (JP)

( * ) Notice: Subject to any disclaimer, the term of this patent is extended or adjusted under 35 U.S.C. 154(b) by 706 days.

(21) Appl. No.: 09/742,338

(22) Filed: Dec. 22, 2000

(65) Prior Publication Data

US 2001/0021266 A1 Sep. 13, 2001

(30) Foreign Application Priority Data

Dec. 22, 1999 (JP) .......................................... 11-365059

(51) Int. Cl.$^7$ ................................................. G06K 9/00
(52) U.S. Cl. ..................................................... 382/162
(58) Field of Search ............................... 382/128–133, 382/162–167; 358/501–540; 600/109–112; 355/35, 69, 77, 84

(56) References Cited

U.S. PATENT DOCUMENTS

| | | | | |
|---|---|---|---|---|
| 5,229,841 A | * | 7/1993 | Taranowski et al. | ........ 356/406 |
| 5,392,067 A | * | 2/1995 | Konno et al. | .................. 348/72 |
| 6,057,866 A | * | 5/2000 | Haneda et al. | .............. 347/118 |
| 6,215,517 B1 | * | 4/2001 | Takahashi et al. | ............. 348/72 |
| 6,275,281 B1 | * | 8/2001 | Nozaki | ......................... 355/35 |

\* cited by examiner

Primary Examiner—Jingge Wu
(74) Attorney, Agent, or Firm—Burns, Doane, Swecker & Mathis, L.L.P.

(57) ABSTRACT

A color image analysis method makes it possible to analyze plural components of a compound individually through formation of an image. Initially, a picture or the image of the compound including the plurality of components is taken by a fluorescence digital image microscope. Then, one or more images of one of the components are extracted or divided from the image of the compound on the basis of color-phase, or color-phase and brightness.

7 Claims, 5 Drawing Sheets

COLOR IMAGE ANALYSIS METHOD

This application is based on and claims priority under 35 U.S.C. § 119 with respect to Japanese Application No. 11(1999)-365059 filed on Dec. 22, 1999, the entire content of which is incorporated herein by reference.

FIELD OF THE INVENTION

The present invention generally relates to color imaging. More particularly, the present invention pertains to a color image analysis method.

BACKGROUND OF THE INVENTION

A known image processing method for analyzing organic components of a resin-including compound involves placing such a compound as a sample material in a fluorescence microscope. Then, a light beam having a first predetermined wavelength is applied to the sample material and the resulting fluorescence produced therein is taken as a picture by a CCD (Charger Coupled Device) camera through an optical filter. Due to the fact that the phenolic plastic components of the sample material are close to each other with respect to the fluorescence wavelength, the aforementioned fluorescence corresponds to at least one of the phenolic plastic components of the sample material. The image taken by the CCD camera is converted into a binary picture or monochrome image as shown in FIG. 7(a) and the resultant image is stored, for later use, in an image processing device. The stored monochrome image is in the form of an intermingled structure of the two phenolic plastic components. The reason is that the foregoing two phenolic plastic components cannot be separated from one another when the image is taken by the CCD camera and so the intermingled structure is, as it is, converted into the monochrome image.

Next, another light beam having a second predetermined wavelength is applied to the sample materiel and the resultant fluorescence produced is taken as a picture by the CCD camera through another optical filter. This fluorescence corresponds to the aramid fiber component of the compound. The image is converted into a binary picture or monochrome image as shown in FIG. 7(b) and is fed to the image processing device.

Then, for purposes of image emphasis, the foregoing two monochrome images are painted with different pseudocolors as shown in FIGS. 8(a) and 8(b). In addition, an analysis of the aramid fiber component is made. Also, as shown in FIG. 9, the distributed condition of all of the components of the compound is displayed by superimposing the image of the aramid fiber component on the image of the intermingled structure of the two phenolic plastic components.

However, in the foregoing analyzing method, when the image of the compound is converted into the binary picture which includes two compounds such as the two phenolic plastic components having closely valued fluorescence wavelengths, the resultant image is a monochrome image in which the two components are intermingled. Thus, individual analysis of each of the components is made rather difficult, if not impossible. As a result, analyzing the foregoing component intermingled image becomes insufficient or unsatisfactory.

Thus, a need exists for a way of establishing an individual analysis of each of the components forming the image of the compound.

SUMMARY OF THE INVENTION

In light of the foregoing, the present invention provides a color image analysis method involving forming an image based on a plurality of components and acquiring an image of each of the components by dividing the formed image on the basis of color-phase.

According to another aspect of the invention, a color image analysis method includes forming an image based on a plurality of components, and acquiring an image of each of the components by dividing the formed image on the basis of color-phase and brightness.

The total occupying area rate of regions of the divided image relative to the whole region of the formed image can be calculated. In addition, the method can involves calculating the occupying area of each of the regions of the divided image can be calculated and calculating frequencies of the occupying areas. In addition, the method can be carried out using a microscope.

With the present invention, because the image formed by the plural components can be divided into an image of each component on the basis of color-phase, it is possible to establish individual analyses of the characteristics of each of the plural components. Also, because the images formed by the plural components can be divided into an image of each component on the basis of color-phase and brightness, it is possible to establish individual analyses of the characteristics of each of the plural components. By calculating the total occupying area rate of each of the regions of the divided image relative to the whole region of the formed image, the content is analyzed by percent of each of the components. By calculating the occupying area of each of the regions of the divided image, the size of each region can be analyzed. Also, by analyzing the frequencies of the occupying areas of each of the divided image, the size distribution condition of the regions is analyzed and obtained. Further, through use of the microscope, the image formed by the plural components can be obtained comparably easily.

According to another aspect of the invention, a color image analysis method involves emitting light towards a target material containing a plurality of components to produce fluorescence in the target material, using the fluorescence to form an image based on the plurality of components and obtain a formed image having color-phase values, using differences between the color-phase values to distinguish a first one of the components in the formed image from a second one of the components in the formed image, and producing a separate image of each of the first and second components using the differences in the color-phase values.

BRIEF DESCRIPTION OF THE DRAWING FIGURES

The foregoing and additional features and characteristics of the present invention will become more apparent from the following detailed description considered with reference to the accompanying drawing figures in which like reference numerals designate like elements and wherein.

Figure 1:
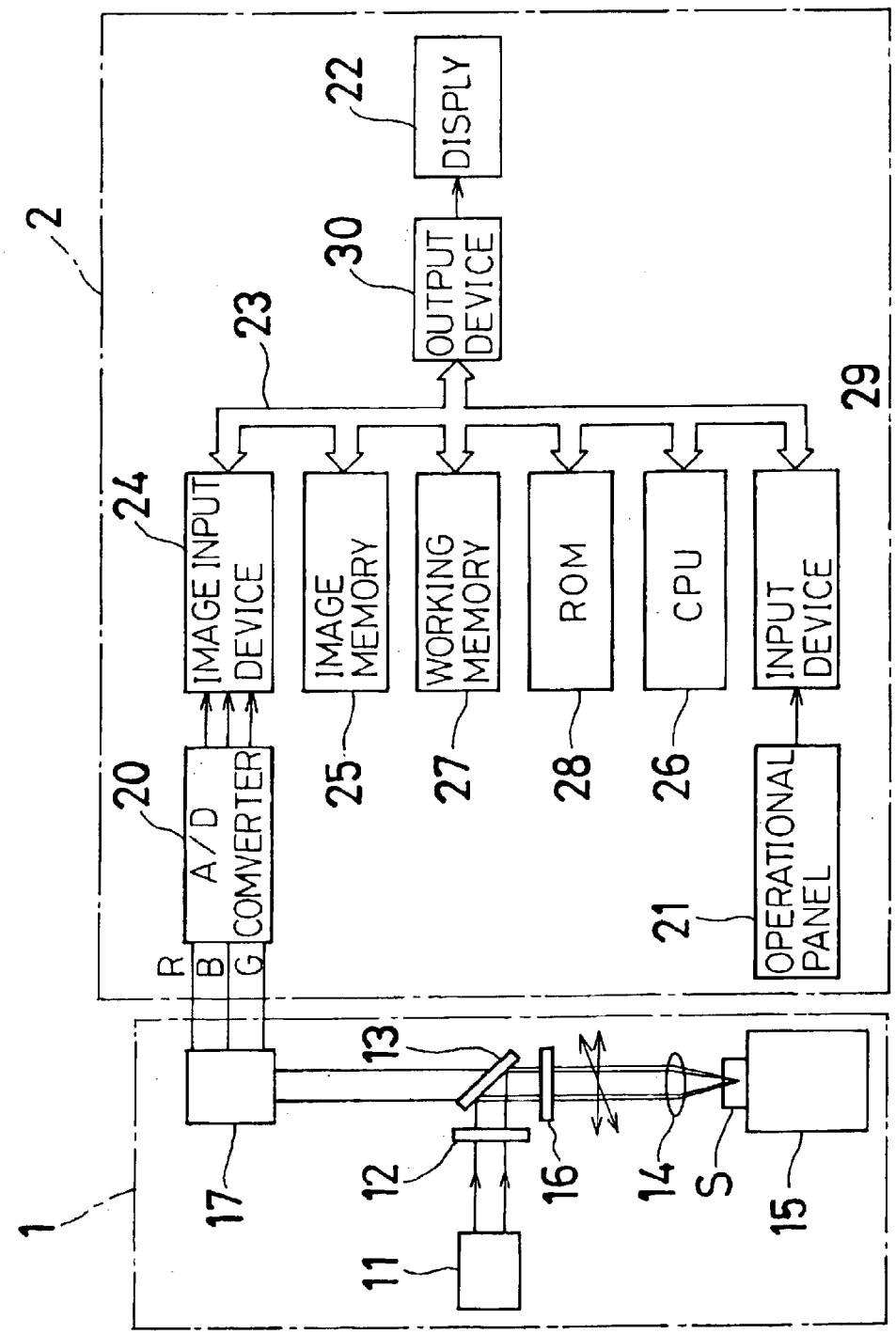
FIG. 1 is a diagrammatic illustration of a color image analysis system in accordance with an embodiment of the present invention.
Figure 5A:
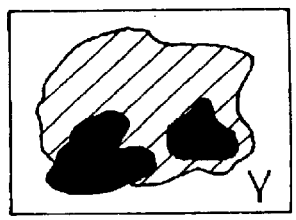
Figure 5B:
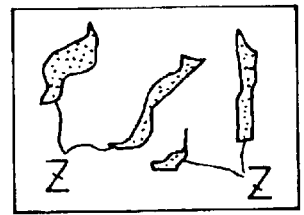
Figure 6A:
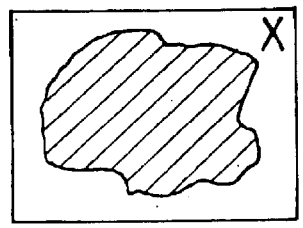
Figure 6B:
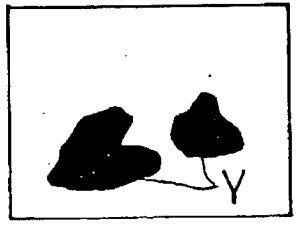
Figure 6C:
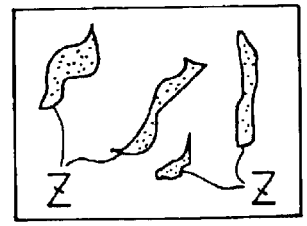
Figure 7A:
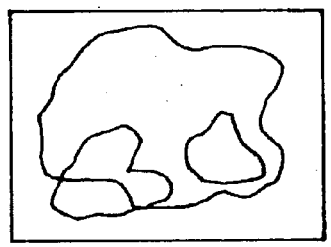
Figure 7B:
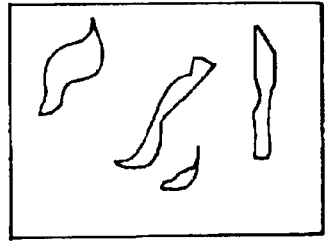
Figure 8A:
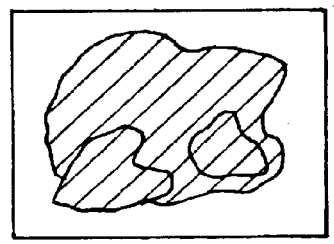
Figure 8B:
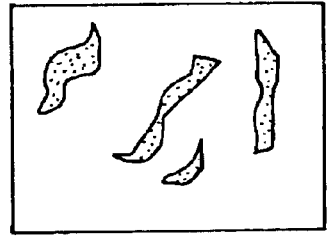
Figure 9:
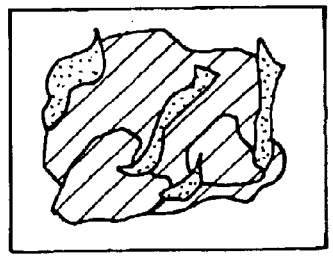

FIGS. 5(a) and 5(b) are pictorial illustrations of observed images of the sampled resin-including compound when using the system shown in FIG. 1;

FIGS. 6(a)–6(c) are pictorial illustrations of observed images of the sampled resin-including compounds when using the system shown in FIG. 1;

FIGS. 7(a)–7(b) are illustrations of observed images of a sampled resin-including compound using a known device;

FIGS. 8(a)–8(b) are illustrations of observed images of the sampled resin-including compound using a known device; and FIG. 9 is a pictorial illustration of an observed image of the sampled resin-including compound using the known device.

DETAILED DESCRIPTION OF THE INVENTION

FIG. 1 illustrates a color image analysis system which is made up of a fluorescence digital image microscope 1 and an image processing device 2 for analyzing an image observed by the fluorescence digital image microscope 1. The fluorescence digital image microscope 1 includes a light source 11, a filter 12, a dichroic mirror 13, an objective lens 14, a stage or platform 15 on which a specimen or target material S is mounted, a fluorescence filter 16, and a 3CCD camera 17 which catches fluorescence emitted from the target material S.

The light source 11 is a device from which a light beam (an exciting light) is emitted to the target material S to produce fluorescence in the target material S. One example of a suitable light source 11 is a mercury lamp.

The filter 12 is designed to allow a certain frequency of the light beam emitted from the light source 11 to pass through the filter 12 so that the fluorescence produced in the target material S falls in a predetermined wavelength range.

The dichroic mirror 13 is a specially designed reflector which reflects the light beam or the exciting light from the light source 11 through an angle of about 90 degrees while also allowing the fluorescence produced in the target material S which has a predetermined wavelength range to pass therethrough toward the 3CCD camera 17 in a straight line fashion. The dichroic mirror 13 having such functions and features enables the objective lens 14 which is designed for observing the target material S to act as a lens for illuminating the exciting light.

The objective lens 14 is thus designed to have the functions of both observation and exciting light illumination, and its magnification is set to be suitable depending on the ingredients of the target material S to be observed.

The fluorescence filter 16 is an optical filter of the band pass type through which passes the fluorescence produced in the target material S only when the wavelength thereof is within the predetermined wavelength band.

The 3CCD camera includes 3 image pick-up elements each of which is made up of a 1600×1200 photo diode picture element matrix array and a CCD resister reading a charged signal generated as a light at each picture element. Color filters of red (R), green (G), and blue (B) which are the primary colors of light regions are assigned to the three image pick-up elements, respectively. Each of the picture element signals which is based on one or more charged signals in the form of light generation at each picture element is fed as an analog signal to the image processing device 2 according to a particular timing.

The image processing device 2 includes an A/D (Analog/Digital) converter 20, an operational panel 21, a display 22, an image input device or image reader 24, an image memory 25, a CPU 26 for executing various calculations and information processing operations, a working memory 27 in which the results of the data processing at the CPU 26 are stored temporally in rereadable fashion, a ROM (Read Only Memory) 28 for storing control programs for the operation of the CPU 26, an input device 29, and an output device 30. The image reader 24, the image memory 25, the CPU 26, the working memory 27, the ROM 28, the input device 29, and the output device 30 are connected to each other by way of a common bus 23.

The A/D converter 20 reads the picture element signals of the respective colors of R, G, and B individually at a particular timing. Each of the picture element signals, depending on its brightness, is converted into a digital signal, for example an 8-bit digital signal. The digital signals corresponding to the specific picture elements of R, G, and B are represented as R(i, j), G(i, j), and B (i, j), respectively. Such digital signals are stored by way of the image reader 24 in the image memory 25 and are forwarded to the working memory 27 for being processed by the CPU 26.

The operational panel 29 is a device at which manipulations or input operations are made and the resulting data is fed or inputted to the input device 29. The operation or processing results by the CPU 26 on the basis of the foregoing data are outputted by way of the output device 30 at the display 22 in the visual mode.

The way in which the component analysis of the target material S is performed using the fluorescence digital image microscope 1 and the an image processing device 2 is as follows. The target material S contains, as its components, a phenolic plastic component X, a phenolic plastic component Y, and an aramid fiber component Z. The outer surface of the target material S is polished in a suitable fashion to a desired or precise degree so that the sample S can be well observed.

Figure 4:
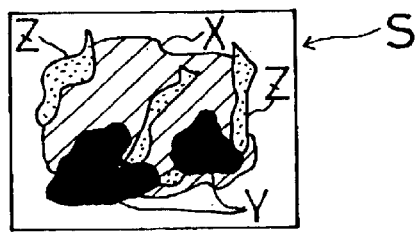
FIG. 4 is a pictorial illustration of an observed image of a sampled resin-including compound when using the system shown in FIG. 1.

When it is desired to analyze all of the ingredients or components X, Y, and Z by concurrent or simultaneous observations, the exciting light filter 12, the dichroic mirror 13, the fluorescence filter 16, and the objective lens 14 are set to, for example, a 450–490 nm wavelength band, a 505 nm wavelength, a 520 nm wavelength, and a ×10 magnification, respectively. At this time, on the basis of each of the digital signals R(i, j), each of the digital signals G(i, j), each of the digital signals B (i, j), and possibly others, an image such as shown in FIG. 4 appears on the display 22. A total analysis is made by displaying such an image in which all of the components X, Y, and Z are intermingled with each other.

When a specific analysis is made by observing the phenolic plastic components X and Y simultaneously, the exciting light filter 12, the dichroic mirror 13, the fluorescence filter 16, and the objective lens 14 are set to, for example, a 450–490 nm wavelength band, a 505 nm wavelength, a 520 nm wavelength, and ×10 magnification, respectively. The reason for the aforementioned concurrent observations of the phenolic plastic components X and Y is due to the fact the fluorescence produced at the phenolic plastic components X and Y, which are red, are very close to each other in fluorescence wavelength. At this time, based on each of the digital signals R(i, j), each of the digital signals G(i, j), each of the digital signals B (i, j), and possibly others, an image such as shown in FIG. 5(a) appears on the display 22. Though this image is in the form of an intermingled mode of the phenolic plastic components X and Y, this image represents or provides color indications of the phenolic plastic components X and Y. Thus, one of the phenolic plastic component X per se, the phenolic plastic component Y per se, and an overlapped portion of the phenolic plastic components X and Y can be distinguished from the others in color-phase and brightness (or luminosity). More specifically, based on the color-phase values C (i, j) which are uniquely defined by or obtained from the digital signals R(i, j), G(i, j), and B(i, j), the phenolic plastic component X per se, the phenolic plastic component Y per se, and the overlapped portion of the phenolic plastic components X and Y are made distinguishable from one another. It is to be noted that the color-phase values C (i, j) are stored in the working memory 27 as 24-bit (3×8-bits) digital values after being calculated based on the 8-bit digital signals R(i, j), G(i, j), and B(i, j).

Figure 2:
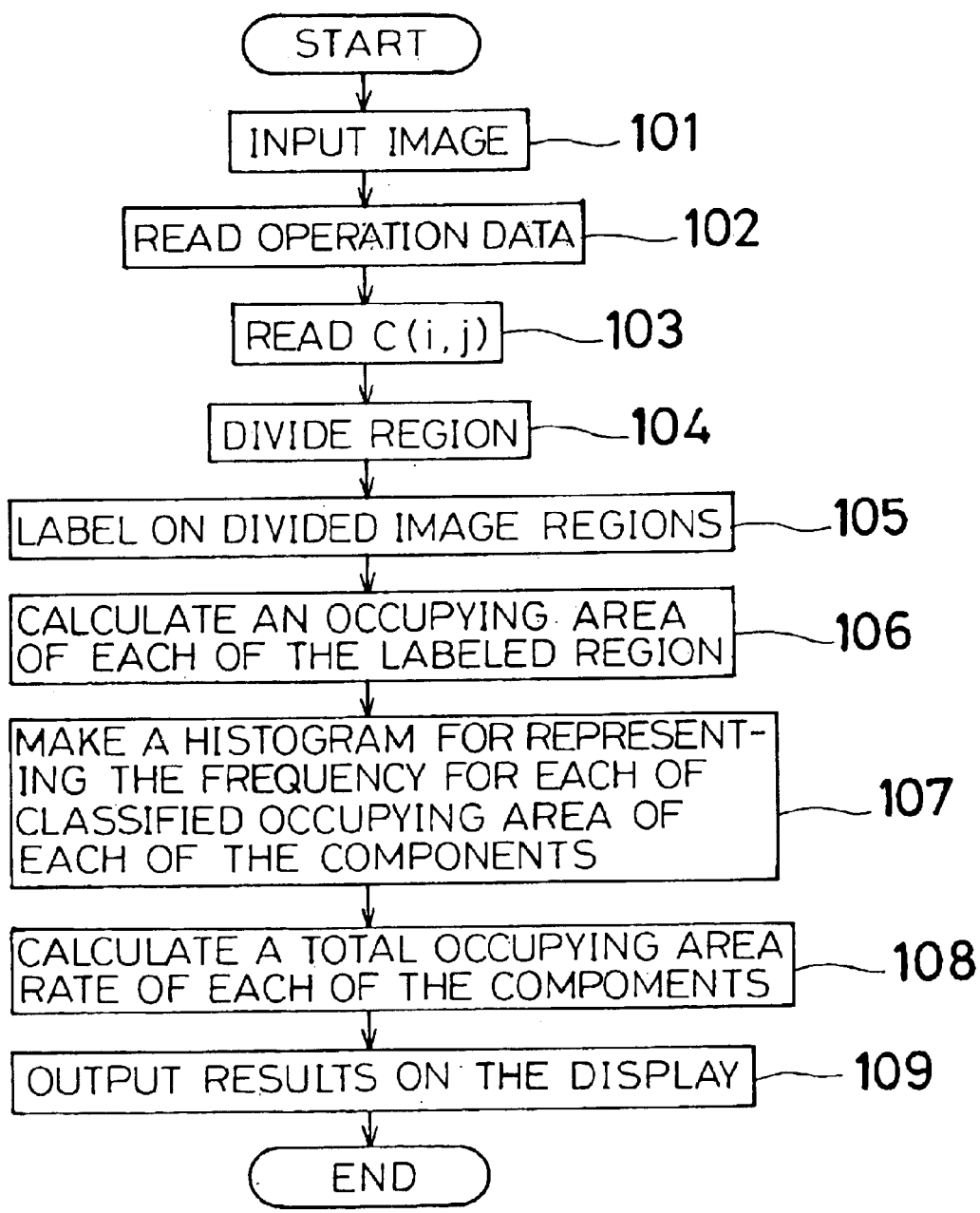
FIG. 2 is a flowchart indicating how the color image analysis is processed.

The analysis of the phenolic plastic components X and Y in an individual fashion in view of the foregoing characteristics is now explained with reference to the flowchart shown in FIG. 2. This analyzing procedure or routine is executed periodically by interruption.

The execution of this routine by the control begins at step 101 at which the CPU 26 reads the digital signals R(i, j), G(i, j), and B(i, j) into the image memory 25 by way of the image reader 24. The routine then proceeds to step 102. At step 102, the CPU 26 reads into the working memory 27 the operation conditions at the operational panel 21 as operation data. Examples of the operation data include, for example, a command specifying the frequency analysis of the occupying area of each of the phenolic plastic components X and Y, a command specifying the analysis of the occupying rate of each of the phenolic plastic components X and Y with respect to the region, and an establishment of distinguishing one of the phenolic plastic component X per se, the phenolic plastic component Y, and an overlapped portion of the phenolic plastic components X and Y from the others on the basis of the color-phase values C(i, j) (color-phase and brightness).

In the present embodiment, when the color-phase value C(i, j) falls in a range C1 the color-phase value C(i, j) is related to only the phenolic plastic component X per se, when the color-phase value C(i, j) falls in a range C2 the color-phase value C(i, j) is related to only the phenolic plastic component Y per se, and when the color-phase value C(i, j) falls in a range C3 the color-phase value C(i, j) is related to the overlapped portion of the phenolic plastic components X and Y. Needless to say, the ranges C1, C2, and C3 are independent of each other, i.e., there is no common factor among the ranges C1, C2, and C3. Thus, analyzing the phenolic plastic component X can be made by analyzing the color-phase values C(i, j) which fall in the ranges C1 and/or C3, while analyzing the phenolic plastic component Y can be made by analyzing the color-phase values C(i, j) which fall in the ranges C2 and/or C3.

The CPU 26, after reading the operation data, proceeds to step 103 to read the color-phase values C(i, j) from the working memory 27 and then proceeds to step 104. At step 104, the CPU 26 performs a region division operation wherein one or more regions occupied by the phenolic plastic component X (Y) are extracted or divided as shown in FIG. 6(a) (FIG. 6(b)) from the image shown in FIG. 5(a) on the basis of the color-phase values C(i, j) which fall in the ranges C1 and/or C3 (C2 and/or C3).

After the aforementioned image region extraction or division, the routine proceeds to step 105 at which the CPU 26 performs labeling on the extracted or divided image regions of the phenolic plastic component X (Y) for pulling out the characteristics of each of the regions. After this labeling, the routine proceeds to step 106 and the CPU 26 calculates an occupying rate of each of the labeled regions. The routine then goes on to step 107.

At step 107, the CPU 26 makes or produces a histogram representing the frequency distribution for each classified occupying area of each of the components of the target material S. Then, at step 108, the CPU 26 calculates a total occupying area rate of each of the components X and Y of the target material S relative to the whole occupying area of the image of the target material S so as to extract a percentage content of each of the components X and Y of the target material S.

After extraction or division of the aforementioned dimensional conditions and the percentage content of each of the components X and Y of the target material S, the CPU 26 goes to step 109 and displays such results on the display 22 by way of the output device 30. Then, the CPU 26 terminates the procedure temporarily. Thus, the phenolic plastic components X and Y of the target material S are analyzed individually or independently.

When a specific analysis is made observing the aramid components Z, the exciting light filter 12, the dichroic mirror 13, the fluorescence filter 16, and the objective lens 14 are set to, for example, a 330–380 nm wavelength band, a 400 nm wavelength, a 420 nm wavelength, and a ×10 magnification, respectively. The fluorescence produced at the aramid components Z is blue. At this time, on the basis of each of the digital signals R(i, j), each of the digital signals G(i, j), each of the digital signals B (i, j), and possibly others, an image such as shown in FIG. 5(b) appears on the display 22. This image is in the form of a color indication which makes it possible to distinguish the aramid component Z from the others, in color-phase and brightness (or luminosity). More specifically, based on the color-phase values C(i, j) which are uniquely defined by or obtained from the digital signals R(i, j), G(i, j), and B(i, j), the aramid component Z is made distinguishable.

Figure 3:
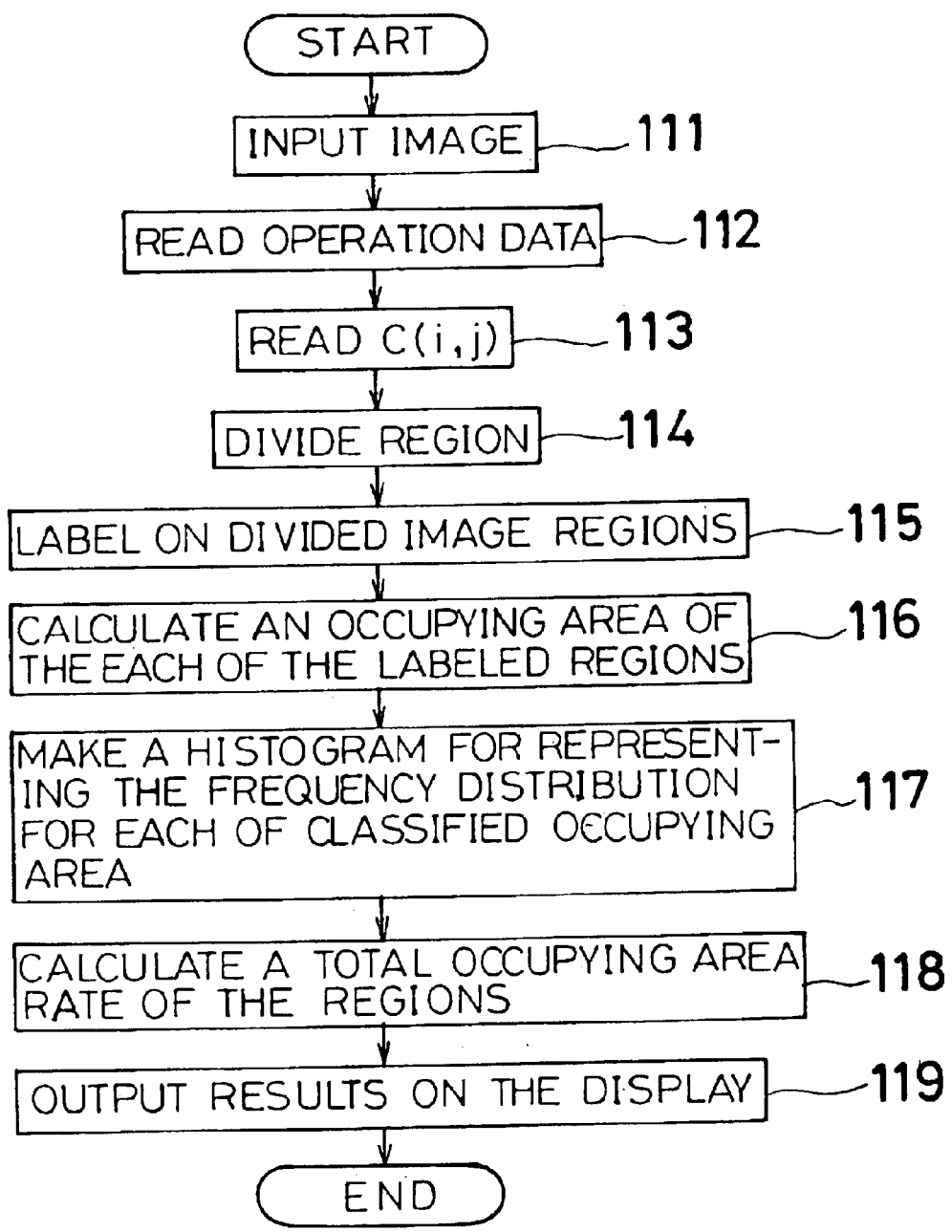
FIG. 3 is a flowchart indicating how the color image analysis is processed.

Considering the aforementioned characteristics of the aramid fiber component Z, set forth below with reference to the flowchart shown in FIG. 3 is an explanation of how the aramid fiber component Z is analyzed in a color image analysis mode. It is to be noted that this routine is also executed by periodic interruption.

When the control begins to execute the routine shown in FIG. 3, initially at step 111, the CPU 26 reads the digital signals R(i, j), G(i, j), and B(i, j) into the image memory 25 by way of the image reader 24. The routine then proceeds to step 112 at which the CPU 26 reads into the working memory 27 the operation conditions at the operation panel 21 as operation data. Examples of the operation data include a command specifying the frequency analysis of the occupying area of the aramid fiber component Z, a command specifying the analysis of the occupying rate of the region of the aramid fiber component Z with respect to the total region of the image, and establishment of distinguishing the aramid fiber component Z from the others on the basis of the color-phase values C(i, j)(color-phase and brightness) falling within the range C3.

After reading the operation data in step 112, the CPU 26 goes to step 113 to read the color-phase values C(i, j) from the working memory 27 and then proceeds to step 114.

At step 114, the CPU 26 performs a region division operation wherein one or more regions occupied by the aramid fiber component Z is extracted or divided as shown in FIG. 6(c) from the image shown in FIG. 5(b) on the basis of the color-phase values C (i, j) which fall in the range C3.

After the aforementioned image region extraction or division, the routine proceeds to step 115 where the CPU 26 makes or produces labeling on the extracted or divided image regions of the aramid fiber component Z for pulling out the characteristics of the aramid fiber component Z. After the aforementioned labeling, the routine proceeds to step 116 where the CPU 26 calculates the occupying area of the each of the labeled regions and then proceed to step 117.

At step 117, the CPU 26 makes or produces a histogram representing the frequency distribution for each of the classified occupying areas of the aramid fiber component Z of the target material S. Next, in step 118, the CPU 26 calculates the total occupying area rate of the regions of the aramid fiber component Z of the target material S relative to the whole occupying area of the image of the target material S to thereby extract a percentage content of the aramid fiber component Z of the target material S.

After extraction of the aforementioned dimensional condition and the percentage content of the aramid fiber component of the target material S, the CPU 26 goes to step 119 and displays such results on the display 22 by way of the output device 30. Then, the CPU 26 terminates the procedure temporarily. Thus, the aramid fiber component Z of the target material S is analyzed.

The present invention provides a number of advantages. The image is divided into each component (the phenolic plastic component X and the phenolic plastic component Y) so as to be separated from one another on the basis of color-phase and brightness (color-phase values C(i, j)). Thus, the characteristics of each of the components can be analyzed individually based on its own image.

In addition, the present invention allows the extraction of various characteristics of each of the phenolic plastic component X and the phenolic plastic component Y, including the occupying area, its frequency (size and condition), and the total occupying area rate relative to the whole area (the percentage content). Also, with the fluorescence microscope 1, the images of the components (i.e., the phenolic plastic component X and the phenolic plastic component Y, and the aramid fiber component Z) of the resin-including compound can be obtained.

In accordance with the present invention, various characteristics of each of the phenolic plastic component X, the phenolic plastic component Y and the aramid fiber compound Z, including the occupying area of each component, its frequency (size and condition), and the occupying area rate relative to the whole area (the percentage content) can be extracted or obtained.

It is to be understood that the description set forth above is not restrictive and various modifications or alternatives can be employed. For example, the operational panel 21 can be designed by using well-known techniques to specify the on-screen scope (whole or part) of analysis, to indicate the size of the compound on the screen depending on the magnification, to specify the center portion when the image is enlarged or reduced, and to order the determination of a distance between two components. Such operations can also be established by manipulating a mouse.

Using well-known techniques, the display can be made to also display, for example, each image in monochrome or three-color synthesis, a scale-varied image, the image within an analytically designated range, the profile image of a region or regions whose brightness is in excess of a value, a label of the region whose brightness is in excess of a value, and a scale related to the on-screen image.

Also, in accordance with the present invention, the color-phase and brightness are defined or determined on the basis of the components (color-phase values C(i, j)) of each of three principle colors, red, green and blue, which are the results of color separation of the color of the image. In addition to this or instead of this, similar definitions of color-phase and brightness can be made with respect to other separated colors such as yellow and violet.

The division of the image of each of the components is made on the basis of the scope in which the color-phase values C(i, j) fall. For the image division, the scope can be stored previously in the ROM 28. In such case, the image division operation can be made automatically.

The above-description describes the division and analysis of the image of the resin-including compound including therein as organic components the phenolic plastic component X and the phenolic plastic component Y. However, division and analysis of the image of any other compound can be made in a similar fashion, such as a resin-including compound including therein as organic components other materials. For example, because it is common that two or more plastic or resin components which are different in denaturing form their own images concurrently, a division of one of such components from the others can be made by application of the present invention. In this case, of course, an individual analysis of each of the two or more plastic or resin components is possible which are different in denaturing.

The present invention can also be applied to dividing and analyzing an image formed on the basis of a specific in-cell structure or an on-chromosome gene having a specific base sequence.

The present invention is described in the context of the observations being made with the fluorescence digital image microscope 1. Instead of the fluorescence digital image microscope 1, other microscopes can be employed such as a universal microscope and a metallographic microscope.

As described above, characteristics of the phenolic plastic component X (Y) include its region occupying area (i.e., the existing condition of size) and the occupying area rate relative to the whole area (i.e., the percentage content). In addition to these characteristics, one or more other characteristics can be extracted. For example, for analyzing purposes, it is possible to extract the peripheral length of each of the regions, the maximum and minimum diameters of each of the regions, the profile or shape of each of the regions, the distance between two adjacent regions, and the center of gravity of each of the regions. When analyzing the profile or shape of the region(s), and to facilitate a successful analysis, well-known image processing techniques can be employed for scale adjustment, shift or movement, and rotation of the image. In addition, for emphasizing the image to be analyzed, well-known image processing techniques such as contrasting the image can be employed.

Moreover, it is possible to analyze the foregoing characteristics in time series, thus making it possible to obtain the changing mode thereof.

As described above, the image of each of the components is extracted on the basis of its color-phase and brightness (i.e. the color-phase values C(i, j)). Instead, the extraction can be made on the basis of only the color-phase (i.e., the fraction rate of each of the digital signals R(i, j), G(i, j), and B(i, j)).

Also, instead of the 3CCD camera 17 having three picture taking plates, a simple CCD camera having a single picture taking plate can also be employed.

In accordance with the present invention, it is possible to establish individual analyses of the characteristics of each of the plural components which form the image. It is also possible to analyze the content by the percent of each of the components. Additionally, the present invention permits an analysis of various characteristics of the components including the size of each region of each component and the size distribution condition of the regions of each component.

Further, with the present invention using the microscope, the image formed by plural components can be obtained relatively easily.

The principles, preferred embodiments and modes of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A color image analysis method comprising:

emitting light from a light source towards a target material containing a plurality of components to cause fluorescence to be emitted from the target material;

using the fluorescence omitted from the target material to form an image based on the plurality of components and obtain a formed image having color-phase values;

using differences between the color-phase values to distinguish a first one of the components in the formed image from a second one of the components in the formed image; and producing a separate image of each of the first and second components using the differences in the color-phase values.

2. The color image analysis method as set forth in claim 1, wherein the light is emitted towards the target sample from a microscope.

3. The color image analysis method as set forth in claim 1, wherein the light is emitted towards the target sample from a fluorescence digital image microscope.

4. The color image analysis method as set forth in claim 1, further comprising calculating a total occupying area rate of regions of the separate images relative to a whole region of the formed image.

5. The color image analysis method as set forth in claim 1, further comprising calculating a total occupying area rate of regions of the separated image relative to a whole region of the formed image.

6. The color image analysis method as set forth in claim 1, further comprising calculating an occupying area of each of the regions of the separated image.

7. The color image analysis method as set forth in claim 3, further comprising calculating frequencies of the occupying areas of the regions of the separated image.

* * * * *